United States Patent
Ristoski et al.

(10) Patent No.: US 12,347,530 B2
(45) Date of Patent: Jul. 1, 2025

(54) EXPERT-IN-THE-LOOP AI FOR MATERIALS GENERATION

(71) Applicant: International Business Machines Corporation, Armonk, NY (US)

(72) Inventors: Petar Ristoski, San Jose, CA (US); Dmitry Zubarev, San Jose, CA (US); Linda Ha Kato, San Jose, CA (US); Anna Lisa Gentile, San Jose, CA (US); Nathaniel H. Park, San Jose, CA (US); Daniel Gruhl, San Jose, CA (US); Steven R. Welch, Gilroy, CA (US); Daniel Paul Sanders, San Jose, CA (US); James L. Hedrick, Pleasanton, CA (US); Chandrasekhar Narayan, San Jose, CA (US); Chad Eric DeLuca, Morgan Hill, CA (US); Alfredo Alba, Morgan Hill, CA (US)

(73) Assignee: International Business Machines Corporation, Armonk, NY (US)

( * ) Notice: Subject to any disclaimer, the term of this patent is extended or adjusted under 35 U.S.C. 154(b) by 465 days.

(21) Appl. No.: 16/835,958

(22) Filed: Mar. 31, 2020

(65) Prior Publication Data
US 2021/0304852 A1    Sep. 30, 2021

(51) Int. Cl.
*G16C 20/70*    (2019.01)

(52) U.S. Cl.
CPC .................................. *G16C 20/70* (2019.02)

(58) Field of Classification Search
CPC ........ G16C 20/70; G16C 20/50; G16C 60/00; G06N 20/00; G06N 20/10; G06N 20/20;
(Continued)

(56) References Cited

U.S. PATENT DOCUMENTS

| | | | |
|---|---|---|---|
| 6,219,622 | B1 | 4/2001 | Schmidt |
| 7,590,517 | B2 | 9/2009 | Doerksen et al. |

(Continued)

FOREIGN PATENT DOCUMENTS

| | | | | |
|---|---|---|---|---|
| EP | 3800586 A1 | * | 4/2021 | ............ G06F 30/13 |
| WO | 2020176164 A1 | | 9/2020 | |

OTHER PUBLICATIONS

U.S. Dept. of Energy. "Workshop on Artificial Intelligence Applied to Materials Discovery and Design," Google, Aug. 2017, pp. 1-76.
(Continued)

*Primary Examiner* — Yoshihisa Ishizuka
(74) *Attorney, Agent, or Firm* — Scully, Scott, Murphy & Presser, P.C.; Caleb Wilkes

(57) ABSTRACT

Candidate material for polymerization can be received. One or more desired features in the candidate material can be identified. A machine learning model can be trained to generate a new material having one or more of the desired features. Permissively, the candidate material can be determined from running a machine learning classification model that ranks a plurality of material as candidates. Permissively, the generated new material can be input to the machine learning classification model, for the machine learning classification model to include in ranking the plurality of material as candidates.

20 Claims, 11 Drawing Sheets

(58) Field of Classification Search
CPC ........ G06N 3/044; G06N 3/045; G06N 3/048; G06N 5/01; G06N 5/02
See application file for complete search history.

(56) References Cited

U.S. PATENT DOCUMENTS

| | | | | |
|---|---|---|---|---|
| 8,612,373 | B2* | 12/2013 | Chidlovskii | G06F 16/35 706/20 |
| 9,462,856 | B2 | 10/2016 | Proud et al. | |
| 9,719,147 | B1 | 8/2017 | Fernandez | |
| 11,087,861 | B2 | 8/2021 | Takeda et al. | |
| 2002/0049548 | A1* | 4/2002 | Bunin | G16C 20/90 702/30 |
| 2003/0134296 | A1 | 7/2003 | Chen et al. | |
| 2006/0074594 | A1 | 4/2006 | Ceder et al. | |
| 2017/0193200 | A1* | 7/2017 | Hsu | G16C 20/30 |
| 2018/0089591 | A1* | 3/2018 | Zeiler | G06F 3/048 |
| 2018/0373980 | A1 | 12/2018 | Huval | |
| 2019/0018933 | A1 | 1/2019 | Oono et al. | |
| 2019/0220573 | A1 | 7/2019 | Kwon et al. | |
| 2019/0304568 | A1* | 10/2019 | Wei | G06N 20/00 |
| 2019/0310207 | A1 | 10/2019 | Guzman Cardozo | |
| 2020/0051671 | A1* | 2/2020 | Maxson | G06N 5/02 |
| 2020/0143903 | A1 | 5/2020 | Sigel et al. | |
| 2020/0294630 | A1* | 9/2020 | Miller | G06N 3/045 |
| 2021/0110891 | A1* | 4/2021 | Fabian | G06N 5/003 |
| 2021/0257049 | A1* | 8/2021 | Abeliuk | G06N 3/045 |

OTHER PUBLICATIONS

Cemicew. "Materials Acceleration Platform—Accelerating Advanced Energy Materials Discovery by Integrating High-Throughput Methods with Artificial Intelligence," Google, Jan. 2018, pp. 1-108.
Anonymous, "New Invented Artificial Intelligence Process Model and Prediction of Assets' Future Values with That," IPCOM000259423D, Aug. 10, 2019, pp. 1-5.
Anonymous, "Applying Machine Learning Techniques to Determine Product Risks," IPCOM000256883D, Jan. 7, 2019, pp. 1-29.
Anonymous, "The Future of Artificial Intelligence in Process Synthesis & Design of Safer Petrochemical Plants," IPCOM000217260D, May 4, 2012, pp. 1-11.
Morgan, H.L. The Generation of a Unique Machine Description for Chemical Structures—A Technique Developed at Chemical Abstracts Service. J. Chem. Doc., Jan. 15, 1965, pp. 107-113.
Degen, J.; et al. "On the Art of Compiling and Using 'Drug-Like' Chemical Fragment Spaces." ChemMedChem. Sep. 15, 2008. pp. 1503-1507.
Batool, M.; et al. "A Structure- Based Drug Discovery Paradigm," Int J Mol Sci 20, Jun. 6, 2019, pp. 1-18.
Bengio, Y.; et al. "Learning Long-term Dependencies with Gradient Descent is Difficult," IEEE Trans Neural Netw, Mar. 1994, pp. 157-166. vol. 5, No. 2.
Brown, D.G.; et al. "Where Do Recent Small Molecule Clinical Development Candidates Come From?" Journal of Medicinal Chemistry. Jun. 19, 2018. pp. 9442-9468. 61, 2.
Cravero, F; et al. "Computer-aided design of polymeric materials: Computational study for characterization of databases for prediction of mechanical properties under polydispersity." Chemometrics and Intelligent Laboratory Systems 191, revised May 18, 2019, accepted Jun. 15, 2019. pp. 65-72.
De Cao, N.; et al. MolGAN: An implicit generative model for small molecular graphs. arXiv preprint arXiv:1805.11973. May 30, 2018. pp. 1-11.
Elton, D. C; et al. Deep learning for molecular generation and optimization—a review of the state of the art. arXiv preprint arXiv:1903.04388. May 22, 2019. pp. 1-24.
Ertl, P; et al. "Estimation of synthetic accessibility score of drug-like molecules based on molecular complexity and fragment contributions." Journal of cheminformatics, Jun. 10, 2009. pp. 1-11.

Goyal, P; et al. Graph embedding techniques, applications, and performance: A survey. Knowledge-Based Systems 151, Dec. 22, 2017. pp. 1-19.
Guimaraes, G; et al. "Objective-reinforced generative adversarial networks (ORGAN) for sequence generation models." arXiv preprint arXiv:1705.10843, Feb. 7, 2018. pp. 1-7.
Hochreiter, S; et al. "Gradient flow in recurrent nets: the difficulty of learning long-term dependencies." Mar. 2003, pp. 1-15.
Huan, T; et al. "A polymer dataset for accelerated property prediction and design." Scientific Data. Mar. 1, 2016, pp. 1-10. 3:160012.
Ishii, M; et al. PoLyInfo RDF: A Semantically Reinforced Polymer Database for Materials Informatics. In Proceedings of the ISWC 2019 Satellite Tracks (Posters & Demonstrations, Industry, and Outrageous Ideas) co-located with 18th Inter-national Semantic Web Conference (ISWC 2019), Auckland, New Zealand, Oct. 26-30, 2019. pp. 69-72.
Kriege, N; et al. "A Survey on Graph Kernels." arXiv preprint arXiv:1903.11835. Feb. 4, 2020, pp. 1-53.
Lin, K; et al. "Adversarial Ranking for Language Generation." 31st conference on Neural Information Processing Systems (NIPS 2017), Dec. 2017, pp. 1-11.
Liu, Y; et al. "Materials discovery and design using machine learning." J Materiomics 3, Aug. 2017, pp. 159-177.
Mannodi-Kanakkithodi, A; et al. "Machine Learning Strategy for Accelerated Design of Polymer Dielectrics." Scientific Reports, Feb. 15, 2016, pp. 1-10, 6:20952.
Patra, T; et al. "Neural-Network-Biased Genetic Algorithms for Materials Design: Evolutionary Algo-rithms That Learn." ACS Combinatorial Science, https://pubs.acs.org/doi/pdf/10.1021/acscombsci.6b00136#. Dec. 20, 2016, accessed Mar. 10, 2020. (Abstract Only). 2 pages.
Rajeswar, S; et al. "Adversarial generation of natural language." arXiv preprint arXiv:1705.10929. May 31, 2017, pp. 1-11.
Rogers, D.; et al. "Extended-connectivity fingerprints." Journal of chemical information and modeling, published on web Apr. 28, 2010, pp. 742-754. 50, 5.
Skalic, M; et al. "Shape-Based Generative Modeling for de Novo Drug Design." Journal of chemical information and modeling. Feb. 14, 2019, pp. 1205-1214. 59.
Smith, J; et al. "Transforming Computational Drug Discovery with Machine Learning and AI." ACS Medicinal Chemistry Letters. Oct. 8, 2018, pp. 1065-1069. 9, 11.
Todeschini, R; et al. "Handbook of molecular descriptors." John Wiley & Sons. Jul. 2008, 20 pages, vol. 11.
Wang, C C; et al. "Computational strategies for polymer dielectrics design." Polymer. Accepted Dec. 29, 2013 and was available online Jan. 14, 2014, pp. 979-988. 55, 4.
Weininger, D. "Smiles, a chemical language and information system. 1. Introduction to methodology and encoding rules." Journal of chemical information and computer sciences. published Feb. 1, 1988, pp. 31-36. 28, 1.
Wu, S; et al. "Machine-learning-assisted discovery of polymers with high thermal conductivity using a molecular design algorithm." npj Computational Materials. Jun. 21, 2019, pp. 1-11. 5, 1.
Yu, L; et al. SeqGAN: Sequence generative adver-sarial nets with policy gradient. arxiv:1609.05473v6. Aug. 25, 2017, pp. 1-11.
Zhang, Y; et al. "Adversarial feature matching for text generation." In Proceedings of the 34th International Conference on Machine Learning. Nov. 18, 2017, pp. 1-10. vol. 70.
Pilania, G; et al. "Accelerating Materials property predictions using Machine Learning." Scientific Reports. Sep. 2013, pp. 1-6, 3:2810.
Xu, H; et al. "A Machine Learning- Based Design Representation Method for Designing Heterogeneous Microstructures." Journal of Mechanical Design. May 2015, pp. 1-11. vol. 137.
Mannodi-kanakkithodi; et al. "Scoping the polymer genome: A roadmap for rational polymer dielectrics design and beyond." Materials Today, Sep. 2018, pp. 785-796. vol. 21, 7.
List of IBM Patents or Patent Applications Treated as Related, dated Mar. 31, 2020, 2 pages.
Chen, T.C., et al., "Generative Deep Neural Networks for Inverse Materials Design Using Backpropagation and Active learning", Advanced Science, 2020, Revised Nov. 11, 2019, Published online Jan. 9, 2020, pp. 1-10, 1902607.

(56) References Cited

OTHER PUBLICATIONS

Duvenaud, D., et al., "Convolutional Networks on Graphs for Learning Molecular Fingerprints", arXiv:1509.09292v2 [cs.LG], Nov. 3, 2015, 9 pages.
Jha, D., et al., "Enhancing materials property prediction by leveraging computational and experimental data using deep transfer learning", Nature Communications, 2019, pp. 1-12, 10:5316.
Office Action dated Oct. 18, 2022 received in U.S. Appl. No. 16/835,892, 53 pages.
Eren, L., et. al., "Generic Intelligent Bearing Fault Diagnosis System Using Compact Adaptive 1 D CNN Classifier", Journal of Signal Processing System, Revised Jan. 18, 2018, Accepted May 7, 2018, Published online May 27, 2018, 12 pages.
Kearnes, S., et al., "Molecular Graph Convolutions: Moving Beyond Fingerprints", arXiv:1603.00856v3, Aug. 18, 2016, 29 pages.
Office Action dated May 5, 2023 recevied in U.S. Appl. No. 16/835,892, 54 pages.
Office Action dated Feb. 9, 2024 received in U.S. Appl. No. 16/835,892, 72 pages.
Notice of Allowance dated Jul. 18, 2024 received in U.S. Appl. No. 16/835,892, 16 pages.

\* cited by examiner

FIG. 4

Accepted — 402

- CCN(C1COC(=O)OC1)C1COC(=O)O C1  
 [View additional chemical info]

- O=C1OCCN(C(=O)C2COC(=O)OC2)CCO1  
 [View additional chemical info]

- O=C1OCC(CC2COC(=O)OC2)CO1  
 [View additional chemical info]

Candidates (535 unknown) — 404

- O=CN(C(=O)C(=O)N(C=O)C1COC(=O)OC1)C1COC(=O)OC1  (Score 98)  
 [View additional chemical info]

- CSC(=O)C1COC(=O)OC1  (Score 98)  
 [View additional chemical info]

- CCC1COC(=O)OC1  (Score 98)  
 [View additional chemical info]

Rejected — 406

- CN(C)CC1COC(=O)OC1  
 [View additional chemical info]

- CNC1COC(=O)OC1  
 [View additional chemical info]

O=C(CCC(=O)NC1COC(=O)OC1)NC1COC(=O)OC1

Top 3 Fragments

[15*]C1COC(=O)OC1 — 502

[5*]N[5*] — 504

[1*]C(=O)CCC([1*])=O — 506

No Similar Chemical SMILES
O=C(CCC(=O)NC1COC(=O)OC1)NC1COC(=O)OC1
(Score 100)

508

Close

FIG. 5

EXPERT-IN-THE-LOOP AI FOR MATERIALS GENERATION

BACKGROUND

The present application relates generally to computers and computer applications, and more particularly to machine learning and polymer materials design and discovery.

Developing new polymers, for example, from initial design through synthesis, scale up, production and delivery to market, can be challenging. It often takes many years to design, synthesize, test, and introduce a new polymer material into the market. Approaches have emerged, such as computational screening, inverse design, generative modeling, reinforcement learning as ways to accelerate the design of polymer materials. The drawback of these approaches is that they generate a large number of candidates for new molecules, which then need to be manually reviewed by subject matter experts who select only a dozen for further investigation.

For example, a challenge in existing approaches is that these approaches tend to generate very large numbers of candidates, often exceeding tens of millions. While the polymers proposed may all meet the material properties desired, there are many additional practical constraints that such approaches fail to consider, for example, synthetic viability, robust polymerization, compliance with internal and external regulations, availability of feed-stock, and/or others. These constraints represent the institutional knowledge, or "chemical common sense" that a human chemist brings to the problem. As a result, a gap exists that separates computer generated candidates from what can actually be realized in an industrial setting.

Subject matter experts (SMEs) such as polymer chemists and synthetic organic chemists review many pages of candidates and select the ones that appear viable for further testing. With the very large number of candidates, and the fact that only a few will be selected for experiment manually, it is likely some viable candidates may be missed in the noise. In addition, the burden of looking through thousands of pages of candidates can be time consuming for the SMEs, and this has become the bottleneck of the computational polymer design approach.

BRIEF SUMMARY

A computer-implemented method and system to accelerate new polymer can be provided. The method and system can accelerate new polymer discovery.

In one aspect, a method can include receiving candidate material for polymerization. The method can also include identifying at least one desired feature in the candidate material. The method can further include training a machine learning model to generate a new material having the at least one desired feature.

In another aspect, a method can include receiving candidate material for polymerization. The method can also include identifying at least one desired feature in the candidate material. The method can further include training a machine learning model to generate a new material having the at least one desired feature. The candidate material can be selected by a subject matter expert.

In yet another aspect, a method can include receiving candidate material for polymerization. The method can also include identifying at least one desired feature in the candidate material. The method can further include training a machine learning model to generate a new material having the at least one desired feature. The candidate material can be determined from running a machine learning classification model that ranks a plurality of material as candidates.

In another aspect, a method can include receiving candidate material for polymerization. The method can also include identifying at least one desired feature in the candidate material. The method can further include training a machine learning model to generate a new material having the at least one desired feature. The candidate material can be determined from running a machine learning classification model that ranks a plurality of material as candidates. The generated new material can be input to the machine learning classification model, for the machine learning classification model to include in ranking the plurality of material as candidates.

In one aspect, a system can include a hardware processor and a memory device coupled with the hardware processor. The hardware processor can be configured to receive candidate material for polymerization. The hardware processor can be further configured to identify at least one desired feature in the candidate material. The hardware processor can be further configured to train a machine learning model to generate a new material having the at least one desired feature.

In another aspect, a system can include a hardware processor and a memory device coupled with the hardware processor. The hardware processor can be configured to receive candidate material for polymerization. The hardware processor can be further configured to identify at least one desired feature in the candidate material. The hardware processor can be further configured to train a machine learning model to generate a new material having the at least one desired feature. The candidate material can be selected by a subject matter expert.

In yet another aspect, a system can include a hardware processor and a memory device coupled with the hardware processor. The hardware processor can be configured to receive candidate material for polymerization. The hardware processor can be further configured to identify at least one desired feature in the candidate material. The hardware processor can be further configured to train a machine learning model to generate a new material having the at least one desired feature. The candidate material can be determined from running a machine learning classification model that ranks a plurality of material as candidates.

In another aspect, a system can include a hardware processor and a memory device coupled with the hardware processor. The hardware processor can be configured to receive candidate material for polymerization. The hardware processor can be further configured to identify at least one desired feature in the candidate material. The hardware processor can be further configured to train a machine learning model to generate a new material having the at least one desired feature. The candidate material can be determined from running a machine learning classification model that ranks a plurality of material as candidates. The generated new material can be input to the machine learning classification model, for the machine learning classification model to include in ranking the plurality of material as candidates.

A computer readable storage medium storing a program of instructions executable by a machine to perform one or more methods described herein also may be provided.

Further features as well as the structure and operation of various embodiments are described in detail below with

BRIEF DESCRIPTION OF THE DRAWINGS

FIG. 4 is a diagram illustrating a user interface (UI) in an embodiment.

FIG. 5 illustrates an example user interface (UI) showing monomer segments exploration and AI explanation in an embodiment.

DETAILED DESCRIPTION

Figure 1:
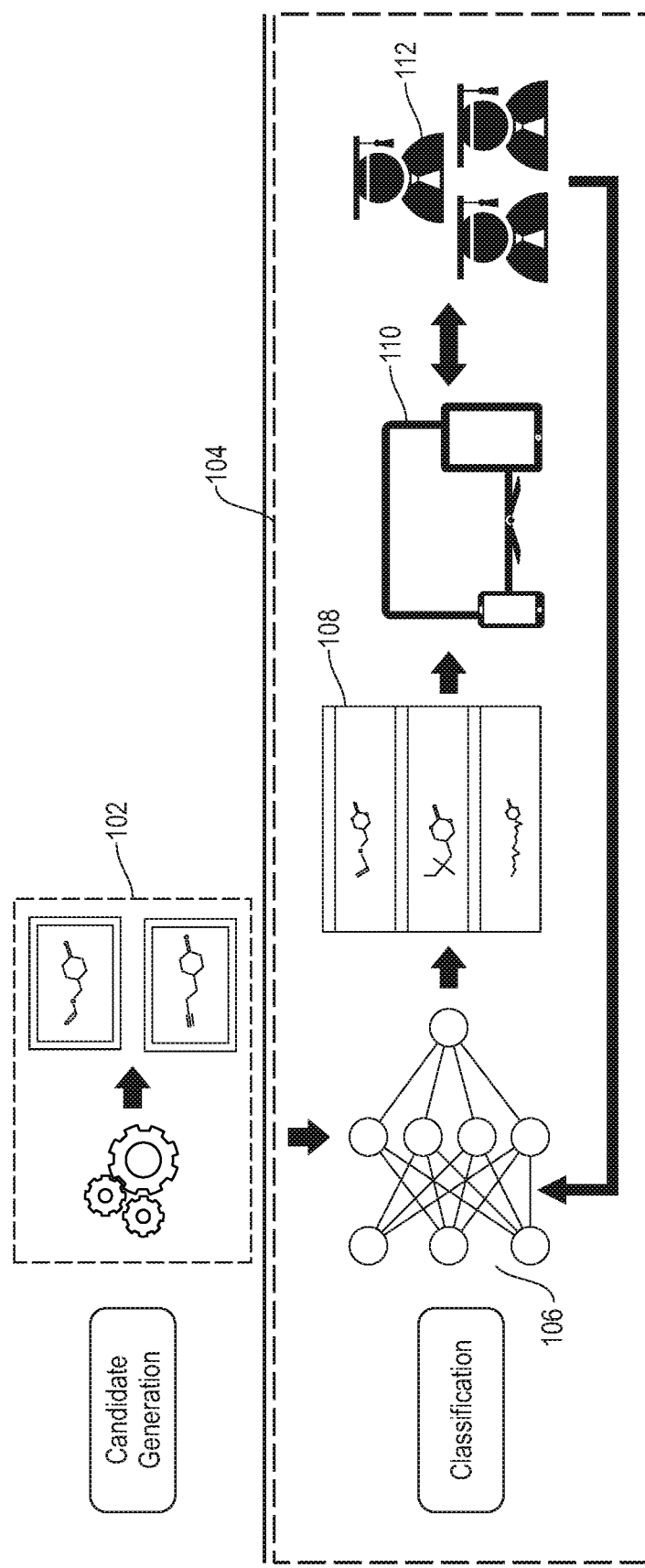
FIG. 1 is a diagram illustrating polymer discovery with expert-in-the-loop workflow in an embodiment.

In an embodiment, a "human-in-the-loop" methodology is presented where the methodology ranks the candidates according to a utility function that is learned via the continued interaction with the subject matter experts, and which is also constrained by specific chemical knowledge.

Polymers are macro-molecules made up of repeating motifs (which themselves can be monomer units in case of homo-polymers or polymer units in case of block copolymers). As materials, they can drive industries from consumer products, such as synthetic fibers, to lithographic processes in microelectronics, to health-care applications. The diversity and appeal of polymer materials for industrial applications stems from the tunable nature of their structure that allows for very finely tuned material properties. Polymer structure can be controlled from the level of monomer selection, combination of monomers, formulation of multiple polymers, processing of the polymer via exposure to various physical factors, such as heat and light, and so on. This can improve efficacy and/or reduce costs and open access to new types of materials.

While existing works use a general synthetic accessibility score as an objective metric (e.g., molecules with low synthetic accessibility score are easy to synthesize), the inventors have recognized that such score does not necessarily correspond with the selection process of trained chemists that work in a laboratory, and that the selection process can even differ between different experts.

In embodiments, the systems, methods, and/or techniques are described for material discovery that can overcome a bottleneck of the computational design approach, for example, by learning from the expert-in-the-loop, and helping the expert-in-the-loop to generate new materials.

In an embodiment, systems, methods and technique (referred to as a methodology for simplicity of explanation) may provide for a discovery of monomers at an early stage defining the structure and properties of the polymer material. A monomer is a molecule that is amenable to polymerization, i.e., a molecule that carries a motif suitable for the specific polymerization reaction and efficiently undergoes polymerization.

Discovery of the monomers in the context of computational chemistry can involve generation of a structural representation of the monomer by means of the computational chemistry tools. The computationally proposed candidates need to be synthesized in the lab and then utilized in the polymer preparation. To assist in the discovery of polymers, the methodology in an embodiment develops a task specific ranking for candidates for a particular polymer that best addresses a particular use case, among a pool of monomer candidates, which has been generated, and which can be very large.

In embodiments, the methodology can provide or implement an expert-in-the-loop artificial intelligence (AI) framework for polymer discovery. In an embodiment, the framework includes a classification model or a classifier, which is trying to capture (or learns) the "institutional knowledge" and preference or bias of the SME for the task of identifying synthesizable monomers in a real laboratory. The SME interacts with a system of the framework through a user interface, and the SME actions are used to update the classification model, for example, in the background. The framework can contain a generative module, which is learning the important features of the accepted monomers in order to generate new novel monomers that follow the SME's selection criteria.

Advantageously, the methodology in embodiments can allow for faster and more accurate processing in polymer discovery and/or generation.

By way of example, the systems, methods, and techniques can be applicable to, but not limited to, fan-out chip design, redistribution layer (RDL) resists, fan-out waver-level packaging (FOWLP), e.g., resists for semiconductors, materials for FOWLP.

FIG. 1 is a diagram illustrating polymer discovery with expert-in-the-loop workflow in an embodiment. The workflow can be executed by one or more computer components, for instance, implemented and/or run on one or more processors or hardware processors, or coupled with one or more hardware processors. One or more hardware processors, for example, may include components such as programmable logic devices, microcontrollers, memory devices, and/or other hardware components, which may be configured to perform respective tasks described in the present disclosure. Coupled memory devices may be configured to selectively store instructions executable by one or more hardware processors.

A processor may be a central processing unit (CPU), a graphics processing unit (GPU), a field programmable gate array (FPGA), an application specific integrated circuit (ASIC), another suitable processing component or device, or one or more combinations thereof. The processor may be coupled with a memory device. The memory device may include random access memory (RAM), read-only memory (ROM) or another memory device, and may store data and/or processor instructions for implementing various functionalities associated with the methods and/or systems described herein. The processor may execute computer instructions stored in the memory or received from another computer device or medium.

In an embodiment, a process or a pipeline of polymer discovery may include generating candidates at 102 and selecting a subset of the candidates at 104, which are viable and practical for being synthesized and polymerized. At 102, the generation of the candidates processing can involve exhaustive enumeration of the molecules that can be built in a combinatorial manner from a library of molecular fragments. A set of reference molecules, such as monomers, is constructed, that were synthesized in practice. For example, the data can be retrieved from the literature or provided by the SME. The reference molecules are split into fragments. The splitting can be done according to the empirical rules taking into account chemical nature of the bonds between motifs, or randomly. Motifs can be as small as individual atoms, functional groups, or combinations thereof. A number of fragments are selected from the fragment library and combined into new molecules; the number of fragments selected and any constraints on their combining, such as compatibility, connectivity, etc., can constitute parameters of the process specified by the user. Generating of candidates at 102 can include additional constraining algorithmic components, for example, including meta-heuristics, such as particle swarm optimization, genetic algorithm optimization, and/or others.

For instance, in an embodiment, the candidate generation at 102 can include, starting from available and already produced monomers, splitting them into fragments which are suitable for the design of new monomers, and generating possible combinations of them that could be suitable for polymerization. The candidate generation can be implemented using different approaches. For example, in an embodiment, the framework uses a set of historically produced monomers to obtain a set of fragments and produce combinations with a defined maximum number of fragments. The defined maximum number of fragments can be predefined, or for example, defined by a user. The SME can constraint the set of fragments to be used, for example, to include polymerizable groups of interest for the specific type of polymer. The result can be a relatively large set of monomer candidates (e.g., several hundred thousand up to several million candidates). Monomer candidates are also referred to as molecule candidates and can include, but not limited to, molecular components and polymer repeat units.

Classification at 104 can include presenting the candidates to an SME. In an embodiment, the generated candidates (e.g., computer-generated candidates at 102), can include molecular components and polymer repeat units. A user interface can be implemented to present the candidates. In an embodiment, the framework may present the candidates initially ordered by their general synthesizability score. In an embodiment, a classification algorithm or model 106, for example, initially outputs the candidates 108, e.g., based on their general synthesizability score. In another embodiment, there may be a general classification algorithm or model that learned general rules for synthesizing new materials that are shared across all labs and SMEs, and the initially presented candidates can be those output by running the general classification algorithm or model.

The candidates can be presented to a specific SME or a specific group of SMEs 112 via a computer user interface 110. As the SME of SMEs 112 adjudicates or selects one or more of the candidates to synthesize, the classification at 104 builds an SME specific model 106 by learning from the SME adjudication. The classification model 106 is built to replicate the specific SME's decision or decisions, for example, to capture the expertise of the SME to aid the selection process. The classification component 104 of the framework can identify "good" monomers, which are viable and practical to synthesize and polymerize, among the candidates. In an embodiment, in this human-in-the-loop methodology, after a few interactions with the SME, the selection can be automated. For example, once the expert (e.g., SME) starts accepting candidates for synthesizing, the classification model 106 is retrained and all (or selected number of) the candidates are re-ranked and shown to the SME in the new order. As the SME adjudicates the candidates, the model is continuously being updated in the background and the candidates are reordered. For example, the classification component 104 can receive SME interaction (e.g., input signaling acceptance and/or rejection) of the candidates and based on the SME interaction the classification component 104 can retrain the classification model 106.

In an embodiment, the material discovery process can start by identifying and formally defining the properties required for the new material. Then, one or more computational approaches (e.g., those rooted in machine learning and/or deep learning) such as combinatorial screening, inverse design, generative modeling, reinforcement learning, and/or others, can be utilized to generate candidate molecular components that are expected to yield materials with target properties. For example, given a set of 200 historically produced monomers, an exhaustive combinatorial enumeration of new monomers yields upwards of approximately $10^7$ candidates. Depending on the target property, the subset of promising candidates may include approximately $10^4$ candidates. For instance, optionally, the combinatorial enumeration of the monomers may be filtered to a smaller subset, for example, based on checking whether the molecules contain a specific fragment. The specific fragment can be one which an SME is looking for. The molecular components that are projected to meet the target property requirement can undergo review by SMEs for selection for the materials synthesis and characterization.

As discussed above, in an embodiment, the methodology may build one general AI model of "synthesizability" across all the users, and a SME (e.g., or SME group) specific AI model for each user (e.g., or user group) in the system. The general model tries to learn general rules for synthesizing new materials that are shared across all labs and SMEs, e.g., each monomer suitable for polymerization must contains a polymerizable group and should not contain pendant groups that will be active under polymerization conditions. The SME-specific model tries to mimic the decision-making process of a single SME (e.g., or a single group of SMEs). By way of example, for both models, the methodology may train a 1 dimensional (D) Convolutional Neural Network. The architecture of the CNN can be (but not limited to): two one-dimensional convolutional layers followed by one max-pooling layer and a fully connected softmax layer. Each convolutional layer can have 100 filters with size 10, using rectified linear unit (ReLU) activation function. The input of the network can be the molecule bit vector produced from the Morgan enumeration of the subgraphs on molecular graphs. Other architectures can be implemented.

In this embodiment, when a new set of material candidates is loaded, the methodology may apply the general model to sort the molecules and present them to the SME for adjudication. As the SME is adjudicating, the system is building a specific model for that SME which is seeking to replicate the SME's decisions. Once the SME-specific model is confident enough (reaches a threshold level of confidence in its prediction), it can be applied on a dataset of candidates for ranking the candidate molecules.

In embodiments, the classification model 106 can be an artificial intelligence model such as Artificial Neural Network (ANN), a Convolutional Neural Network (CNN), Random Forest (RF), Support Vector Machines (SVM), Logistic Regression (LR) and/or another. The classification model 106 is trained to identify synthesizable monomers that are suitable for the expert. The classification model's (or the classifier's) confidence or confidence score can be used to order the monomer candidates.

In embodiments, the polymer discovery process may include using a data representation or format, for representing chemical structure or molecule graph. In an embodiment, the data representation uses feature vector representation (propositionalization) of molecule graph. A vectorized data representation can allow scaling to real world sized chemical datasets. Working with such data representation can increase the computation runtime. Different approaches can be used to generate a feature vector from the monomer molecules: e.g., (i) topological fingerprints for molecular characterization and (ii) molecular fragments. The advantage of such propositionalization strategies is that they are computationally inexpensive and once the vectors are extracted, any standard algorithm can be used on the data for the further processing, e.g., on the following steps in the polymer discover and/or generation pipeline.

Molecular Fingerprints: Molecular fingerprints are representations of molecule structures originally designed to assist in chemical database substructure search, but later used for various
  analysis tasks and machine learning applications. The molecular fingerprints follow the idea of applying graph kernels on an input graph in order to generate a feature vector for the graph. An embodiment of the methodology can use the Extended-Connectivity Fingerprints (ECFPs), which are a novel class of topological fingerprints for molecular characterization. ECFPs are circular fingerprints that can be rapidly calculated and can represent an infinite number of different molecular features. The features in the ECFPs represent the presence of particular molecular substructures. The ECFPs can be calculated in 3 steps. First, each atom is assigned a unique integer identifier. Second, each atom identifier is updated with the identifiers of its neighbors. A hash function is used to reduce the concatenated identifiers back into a new, single-integer identifier for each atom. All the atoms are being relabeled with the new identifiers, and the steps are being repeated n times, where n is the radius. In the final step, all duplicate identifiers are removed, and the remaining identifiers define the ECFP fingerprint. The fingerprint represents a bit vector, which can be used for data analysis and machine learning. For example, the vector can be used to calculate similarities between molecules (e.g., using cosine similarity), and as a feature vector for classification.

Monomer Fragments: There are several existing approaches that are able to decompose the molecules into fragments. During fragmentation, the molecule is cut at specific bonds and with that converted in a set of fragments. To be able to carry an efficient and effective fragmentation a set of rules and filters can be defined. An embodiment of the methodology can use an approach, which provides an elaborate set of rules for the breaking of retrosynthetically interesting chemical substructures (BRICS). The algorithm takes on an input a SMILES (Simplified Molecular Input Line Entry System) string for a molecule, and outputs a set of unique fragments, where the order of the fragments is preserved. For example, the SMILES string CC(C)C1(NC(=NC(=O)On2cc[n+](CCCCCCCOC=O) c2)NC2COC(=O)OC2)COC(C)(C)OC1 can be fragmented in the following set of fragments {[1*]C(=O)N=C(N[5*])N[5*], [3*]OC=O, [15*]ClCOC(=O)OC1, [3*]Onlcc[n+](CCCCCCC[4*])c1, [4*]C1([15*])COC(C)(C)OC1, [8*]C(C)C}. Such representation of a molecule can be used as a feature vector in machine learning algorithms, e.g., it can be used as a bag-of-words with TF-IDF weighing. Furthermore, as the order is preserved in the set of fragments, the methodology can consider such representation of a molecule as if it was a sentence, and thus use many existing NLP models directly on molecules. For example, as further discussed below, an aspect of a methodology can use the BRICS representation for training Generative Adversarial Networks for text generation, or molecule generation. The set of fragments can be converted back to the original molecule.

Other data representation and transformation strategies, e.g., graph kernels or graph embedding approaches can be used, to capture molecule properties that can be fed in machine learning algorithms.

By way of example only, a training data set to train or build the classification model 106 can include a random sample from a combinatorial library of polymerizable components suitable for the preparation of polyimides, including dianhydrides, dicarboxylic acids, and diamines. The training data set can be annotated by an SME or a group of SMEs. To evaluate the classification model built on such data, another data set such as a random sample from a combinatorial library of monomers for ring opening polymerization can be used. Other training and evaluation data sets can be used.

Figure 2:
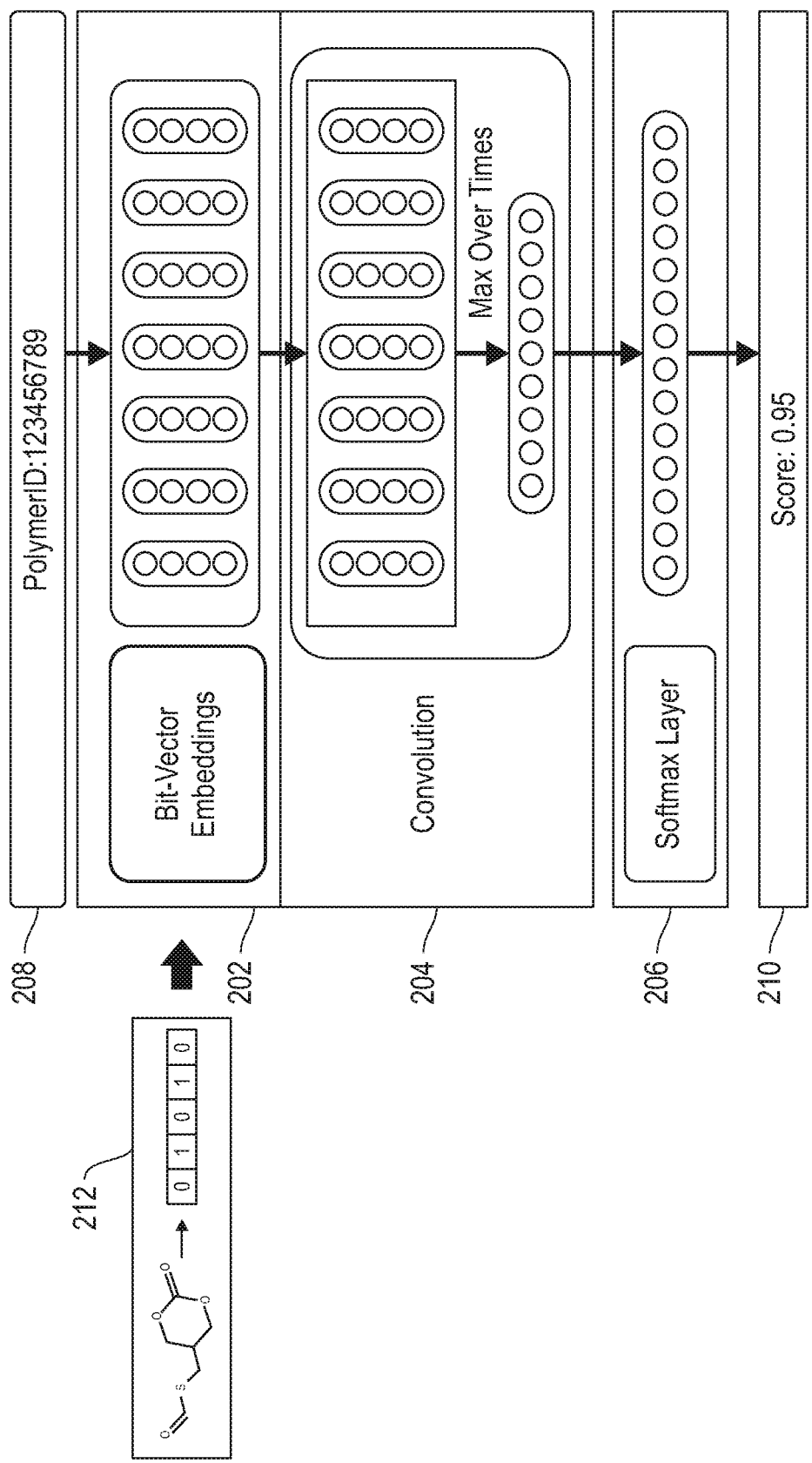
FIG. 2 shows example architecture of a classification model in an embodiment.

FIG. 2 shows example architecture of a classification model in an embodiment. For instance, the classification model (shown in FIG. 1, 106) can be a convolutional neural network (CNN) model. A chemical structure 212 can be converted into a unique machine description, for example, a structural fingerprint. In a particular example, the CNN can include a bit-vector embedding matrix in an embedding layer 202, convolution layers 204 (e.g., 3×1-dimensional convolutional layer with rectified linear unit (ReLU), 100 filters with size 10, and max pooling layer), and a fully connected softmax layer 206. The CNN can perform feature extraction and combinations in each of its layers, for example, to identify strong patterns on what makes a monomer a good candidate for synthesis. The CNN can be trained to output a score 210, e.g., a confidence score, associated with a monomer candidate, for polymerization into a particular polymer. For example, a monomer or another molecular component identified by a unique number or identification (ID) 208 can be input to the CNN, for which the corresponding bit-vector from 212 can be loaded in 202. The CNN outputs a score 210 associated with the input monomer or component. The classification can use the classifier's (classification model's) confidence score to order the monomer candidates. The molecular fingerprints can be considered as an embedding of the molecule, e.g., represented as a bit-vector embedding matrix shown at 202. The molecular fingerprints can be used to train the CNN. For instance, the input of the CNN can be the molecule bit vector produced from the Morgan enumeration of the subgraphs on molecular graphs.

For example, the CNN can be trained to predict that a specific SME would select a given monomer for synthesizing into a polymer having desired target properties. For instance, the CNN outputs a score 210 for a candidate monomer 212 represented in a feature vector data representation format, the score 210 representing the probability that the specific SME would select the candidate monomer 208 for synthesizing into the polymer having desired target properties. The CNN is retrained based on the SME interaction. For example, the characteristics of monomers (such as fragments of monomers), which the particular SME or group of SMEs have chosen and/or not chosen can be used by the CNN to retrain its selection or ranking process. For instance, each time the SME accepts or rejects a monomer, the CNN learns which features (e.g., represented as on/off bits in feature vector data representation) of a monomer are desirable and/or which are not.

As another example, the classification model can be a 1-dimensional CNN. For instance, the architecture of the CNN can include four one-dimensional convolutional layers followed by one max-pooling layer and fully connected softmax layer. Each convolution layer can have 100 filters with size 10, using ReLU activation function. Other CNN architectures can be implemented and used.

Yet as another example, in one or more other algorithms which implement a classification model (e.g., shown in FIG. 1, 106), the classification component 104 can use TF-IDF bag-of-words representation using the molecular fragments. By way of example, a Random Forest (RF) implementation of the classification model can include Random Forest with 100 decision trees.

In another aspect, a polymer generation framework can be provided. For example, artificial intelligence networks such as generative adversarial networks can be implemented to generate additional monomers as additional candidates, for instance, based on using accepted candidates accepted by a specific SME or a specific group of SMEs. The generating process can produce monomers that are outside of the initial combinatorial space. The candidate generation can be performed with different approaches. In an embodiment, the candidate generation (e.g., shown at 102 in FIG. 1) and classification (shown at 104 in FIG. 1) can be iterated, using the accepted candidates from the classification as positive examples, to generate potential monomer solutions.

Figure 3:
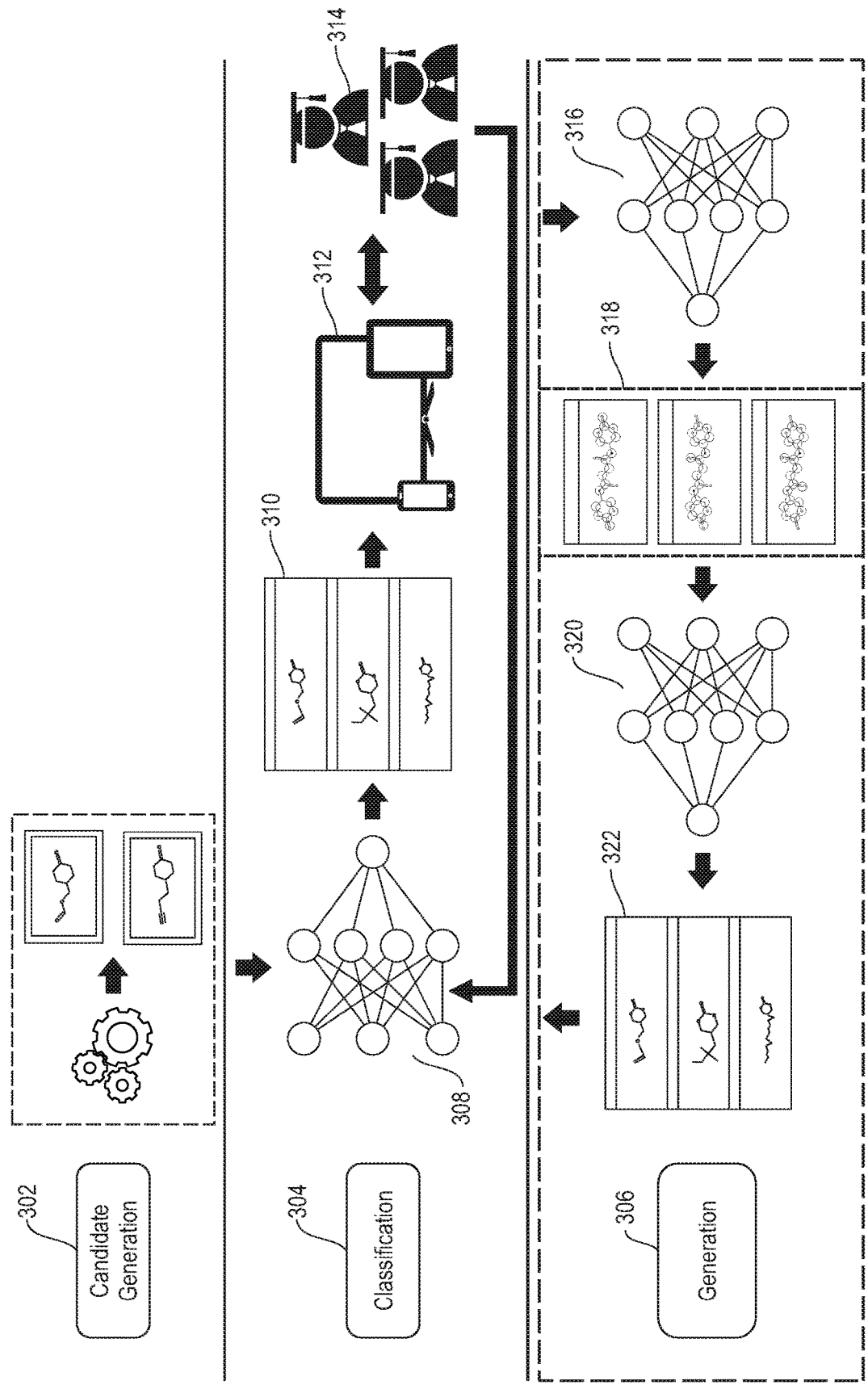
FIG. 3 is a diagram illustrating a pipeline for polymer generation in an embodiment.

FIG. 3 is a diagram illustrating a pipeline for polymer generation in an embodiment. Candidate generation at 302 can be similar to the candidate generation described above with respect to FIG. 1 at 102. For instance, a set of historically produced monomers can be used to obtain a set of fragments and to produce combinations with a defined maximum number of fragments. An SME can constraint the set of fragments to be used, to include polymerizable groups of interest for the specific type of polymer. The result is a relatively large set of monomer candidates.

Classification or ranking at 304 can be similar to the classification described above with respect to FIG. 1 at 104. For example, an artificial intelligence model or network can be trained or implemented to identify one or more monomers, which are viable and practical to synthesize and polymerize, among the candidates. Examples of artificial intelligence models can include, but are not limited to, Artificial Neural Network (ANN), a Convolutional Neural Network (CNN), Random Forest (RF), Support Vector Machines (SVM), Logistic Regression (LR) and/or another. A classification model 308 is trained to identify synthesizable monomers that are suitable for a particular or specific SME or group of SMEs 314. The classification model's (or the classifier's) confidence or confidence score can be used to order the monomer candidates. For example, a classification algorithm or model 308 can initially outputs the candidates 310. The candidates can be presented to a specific SME or a specific group of SMEs 314 via a computer user interface 312. As the SME of SMEs 314 adjudicates or selects one or more of the candidates to synthesize and/or polymerize, the classification at 304 builds an SME specific model 308 by learning from the SME adjudication. For example, the classification model 308 may learn through a continuous interaction with the SME 314 to identify synthesizable monomer in a set of candidates.

In an embodiment, a generation processing 306 tries to generate monomer candidates which have similar features and properties to the accepted or selected candidates. For example, once the SME 314 has accepted a set of monomer candidates, this module 306 tries to generate novel monomer candidates which have similar features and properties to the accepted candidates. In an embodiment, the generation processing 306 may use the molecular fragments representation, where each molecule is represented as a set of fragments. This representation is similar to a sentence, where each fragment can be considered as a word in a sentence. Using this representation, the generation processing 306 may implement standard text generation approaches to generate new monomers.

A machine learning model 316 can be trained to look for important features 318 associated with given one or more monomers, for example, those selected by an SME at 314. Using the trained model 316, extracted features of the candidate structures determined to be important can be presented or visualized, for example, on a user interface.

For example, each candidate monomer can go through a random forest model, which is able to identify feature relevance. The random forest model can be trained on a set of accepted and rejected monomers. Then given any monomer, the model can identify which fragments of the monomer might be of interest for the SME, or which fragments the SME previously considered the most important. To train the random forest model, the methodology in an embodiment can use the BRICS representation. In an embodiment, candidate structures (e.g., structures accepted by the SME) can be decomposed into fragments according to BRICS. Each molecule can be converted in a TF-IDF vector of fragments. The random forest model with a number of decision trees can be implemented (e.g., 100 decision trees). The random forest model is used to extract rules and features. The features can be visualized for the SME. With such a representation, the methodology can analyze all the trees in the random forest model to identify which BRICS fragments are the most relevant for the monomer (e.g., given monomer and/or one being classified as positive).

In an aspect, identifying desired features or important features (e.g., as done at 316) can provide an explainable AI, for instance, for SME decision making. FIG. 5 illustrates an example user interface (UI) showing monomer segments exploration and AI explanation in an embodiment. For example, top 3 fragments 502, 504, 506 for each monomer 508 can be presented in the UI. In an embodiment, the SME can be allowed to select all the BRICS fragments that must be included in the generation process, e.g., biasing the generative models. The visualization and the conversion to different formats of the monomers can be done using existing cheminformatics software.

Referring to FIG. 3, sequential neural network and Generative Adversarial Network (GAN) are some example techniques (but not limited to such) for implementing a model 320 for generating monomers at 306 based on the important features 318. The following illustrate examples. Long short term memory (LSTM) neural networks are special type of recurrent neural networks (RNN), which can be used in NLP application. RNNs are able to model sequential data with temporal dependencies, like text. RNNs perform the same task for every element in a sequence, e.g., word in a sentence, conditioning the output of the model on the previous computations. LSTM networks are capable of learning long-term dependencies. As the LSTM networks perform well on analyzing sequences of values and predicting the next one, they have been successfully applied for the task of text generation, i.e., given a sequence of words, the model can successfully predict the next word in the sequence. Bidirectional LSTMs (BiLSTM) are an extension of the traditional LSTMs, which are able to capture the backwards dependencies in the sequential data. Instead of training one LSTM model the BiLSTMs train two models, one for the data in the original direction, and one for the reversed copy of the input sequence.

SeqGAN is a Sequence Generative Adversarial Network using reinforcement learning. The system includes generator and discriminator, where the generator is treated as reinforcement learning agent. In such a scenario, the generated tokens represent the state and the action is the next token to be generated. The reward can be calculated by the discriminator on a complete sequence via Monte Carlo search.

RankGAN is an adversarial learning framework which includes a generator module and a ranker module rather than a discriminator. Instead of performing a binary classification on the generated samples, RankGAN performs learning-to-rank optimization to rank the machine-generated samples lower than the human-generated samples. On the other hand, the generator is being trained to generate samples that will force the ranker to rank the machine-generated samples higher than the human-generated samples.

TextGAN uses simple GAN architecture, where the generator is an LSTM network, and the discriminator is a convolutional neural network (CNN).

By way of example, an LSTM network implementing the model 320 can include 4 stacked 256-unit LSTM layers, each followed by dropout layer with probability of 0.2 where the last layer is a fully connected softmax layer. Default parameters can be used in implementations using one or more of SeqGAN, RankGAN and TextGAN. The models can be implemented in TensorFlow, for example.

Training data for training monomer generation model 320 can include monomers (e.g., desired fragments extracted from the monomers) that are accepted by the specific SME or SMEs, for example, from the list of candidates the classification model 308 selected. Other training data can be used. For example, a model at 316 can extract desired fragments and the model at 320 can integrate SME defined constraints (e.g., length, atoms and additional properties), and generate sequences of fragments. For example, the model 320 can be a GAN model which generates new examples that have similar features as the accepted monomers. In another aspect, in cases where the SME specifies to lock or include a specific feature (e.g., some specific ring in the molecule), such specification can be put as a constraint in the generative model, to make sure that the model will generate only monomers that contain that specific feature. A valid molecular structure from the sequence of fragments can be recompiled, for example, using BRICS.

The generated monomers (e.g., molecular structure) can be fed to the classification model 308 for ranking or selection as possible candidate monomers to present to the SME 314. The generated monomers or molecules can be presented at 322 on a UI.

In another aspect, the generation processing 306 can run independently of the polymer discovery pipeline at 302 and 304. For instance, the module at 306 can receive as input one or more candidate monomers, which can be SME selected candidates, to perform the generation processing, without necessarily needing to connect to the generation 302 and classification 304. For example, candidate monomers can be received and a model at 316 (trained to extract desired or important features) can be run to extract features from the candidate monomers. The extract features can be presented, e.g., as shown at 318. Based on the extracted features, the trained model (e.g., a deep machine learning model) 320 can be run to generate monomers or molecules having new features. The model 320 can be trained as discussed above, for example, based on a data set representing viable monomers for synthesizing. The generated monomers or molecules can be presented at 322 on a UI.

In an aspect, the model at 320 (e.g., generative model) tries to generate new monomers that follow the distribution of properties in the set of positive monomers, which for example, corresponds to the general objective of the SME(s). In another aspect, to allow an SME to be able to explore new fragments and new type of monomers, an exploratory user interface can be provided to allow the SME(s) to adjudicate the fragments of the monomers, and initiate a generation process using their preferred fragments. To do so, the reinforcement policy associated with the model can be updated to explicitly increase the reward for the fragments selected by the SME.

The module at 306 includes a model for generating new materials. In an embodiment, there can be an expert-in-the-loop. For example, an algorithm including the following steps can run in iterations: identifying desired features; generating new material; and ranking and adjudication. To identify the desired features, the module 306 tries to identify patterns in the materials, e.g., already selected by the SME, or given as input. For example, a classification model such as shown at 308 can be run to identify the top-N positive instances and top-N negative instances. The module 306 may decompose the materials into a set of fragments using standard chemoinformatics approaches, and generate TF-IDF vector for each instance in the dataset. The dataset can be then fed into another model, e.g., a Random Forest model with a number of (e.g., 100) decision trees. The resulting model is used to identify the strongest patterns in the dataset, which are the desired features of the material.

Once the desired features are identified, the module at 306 may use sequence generative adversarial deep neural network (e.g., 320) to generate new materials. The model 320 can be trained on all the historic data, for example, a set of adjudicated examples by the SME. Such an approach may ensure that the desired properties will appear in the newly generated materials, the materials are synthesizable in the lab, and they introduce a level of creativity, which may lead to unexpected discoveries.

By way of example, a GAN model can be built to implement the model 320. The GAN model can include a generator and discriminator. The generator uses the adjudicated examples to identify patterns in the positive examples, and tries to generate new examples that follow the same patterns. The input of the generator is the set of adjudicated examples. The newly generated examples, as well as the examples that were already accepted by the SME go into the discriminator. The discriminator tries to identify which examples are coming from the real data (the ones that the SME accepted) and which are being generated by the generator. If the discriminator can easily identify the examples generated by the generator, that means that they are far from the real-world examples and are probably not very good. Using reinforcement policies the feedback from the discriminator is being passed back to the generator. The generator and discriminator are in kind of reinforcement relationship and improve each other over time. The goal is for the generator to generate new synthetic examples that cannot be distinguished from the real-world examples.

While by design, the GAN network should learn the desired features based on the positive examples provided, the methodology in an embodiment can interfere with the generation process by locking the desired fragments of the molecule. For example, the methodology may implement the GAN's generator to always include the fragment [3*] OC=O in all the monomers that it will generate. This can be done, for example, by rejecting all examples that do not contain this fragment, or by manually updating the reward that the discriminator gives to the generator. The reward indicates how good the generated example is.

A different machine learning model or architecture can also be implemented.

The generated materials can be ranked and presented to the SME. The SME may continue with the adjudication and can initiate new iteration.

FIG. 4 is a diagram illustrating a user interface (UI) in an embodiment. The user interface may be implemented as a Web application. The user interface shows an example monomer ranking presentation to an SME, e.g., at 112 in FIGS. 1 and/or 314 in FIG. 2. The candidates are listed in the middle column 404, ordered by the classifier confidence. Each candidate is represented with the corresponding SMILES string and the 2D representation of the molecule structure. The users (e.g., SMEs) may accept (e.g., left arrow) or reject (e.g., right arrow) the candidates. Other input elements can be implemented and used for indicating acceptance and rejection. The first column 402 shows accepted structures. The third column 404 shows rejected structures. In an embodiment using the user interface, the user need not be exposed to the backend (e.g., AI, machine learning processing and modeling), but interacts with the UI only, and thus requires no deep understanding of the underlying AI systems.

Figure 6:
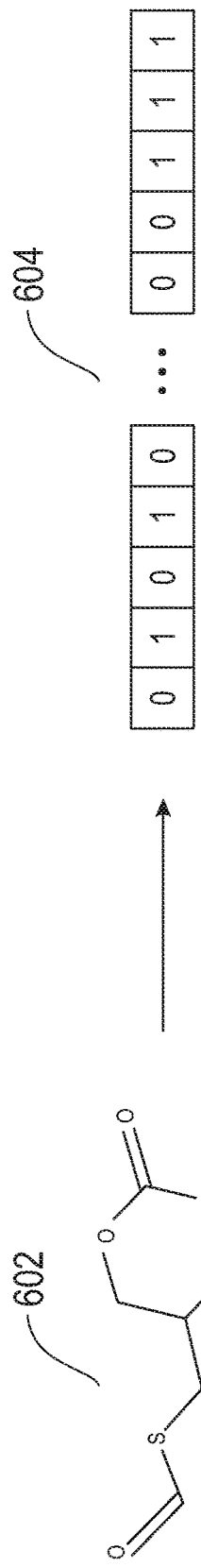
FIG. 6 illustrates an example of molecular fingerprint in an embodiment.

FIG. 6 illustrates an example of molecular fingerprint in an embodiment. For example, a kernel function can be applied to a molecule 602 to generate a bit vector fingerprint (presence/absence of the structural motifs) 604. Generally, a kernel function transforms the input data in a feature space. Graph kernels are used to convert graphs, or sub-graphs, into a feature vector in a new feature space. In this example, a molecular graph is being converted to an array of bits. For instance, standard kernels extract features of the molecule, hash them, and use the hash to determine bits that should be set. An example fingerprints sizes range from 1,000 (1K)-4,000 (4K) bits. In an embodiment, Morgan Fingerprint techniques can be used to generate identifiers.

Figure 7:
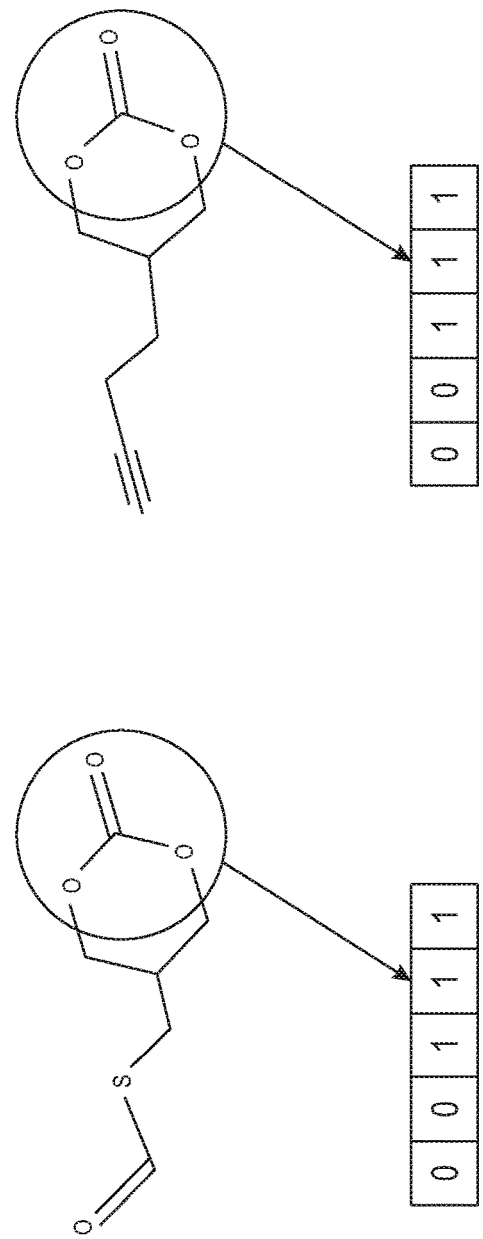
FIG. 7 illustrates an example showing fingerprint similarity in an embodiment.

FIG. 7 illustrates an example showing fingerprint similarity in an embodiment. Each fingerprint bit can correspond to a fragment of the molecule. Molecules that share many fragments are more similar. Fingerprints can be used as feature vectors for machine learning. For example, polymers can be clustered based on similarity of their fingerprints. AI models, for example, classification at 106, 308, 322 may leverage such fingerprint similarity in their training and prediction.

Figure 8:
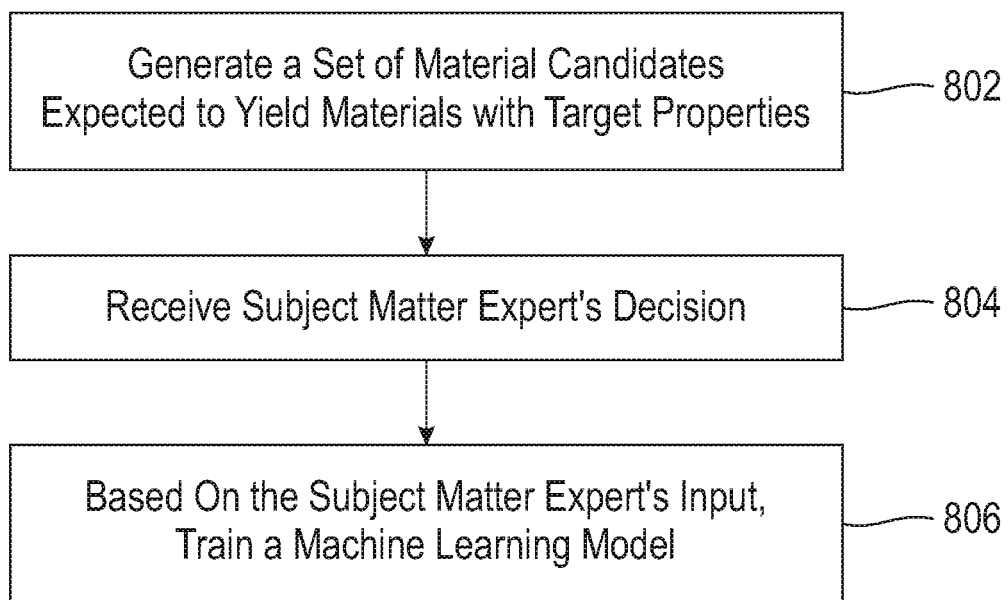
FIG. 8 is a diagram illustrating a method of polymer discovery in an embodiment.

FIG. 8 is a diagram illustrating a method of polymer discovery in one embodiment. The method can be performed on one or more hardware processors. The method in an embodiment learns to rank candidate monomers for polymerization. At 802, the method can include generating a set of material candidates expected to yield materials with target properties. Examples of material candidates include, but not limited to, molecules, monomers, and/or polymer repeat units.

At 804, the method can include receiving subject matter expert's decision indicating accepted and rejected material candidates from the set of material candidates.

At 806, the method can include, based on the subject matter expert's input, training a machine learning model to replicate the subject matter expert's decision, for example, to select material candidates taking into account the subject matter expert's criteria or decision making process. For example, properties and/or fragments contained in the accepted material candidates can be taken into account. In an embodiment, the training can include, applying the trained machine learning model to the generated set of material candidates. The trained machine learning model can output a ranked list of candidates (e.g., by score). A subset of the ranked list (e.g., top n number of candidates) can be presented to the subject matter expert to adjudicate on the machine learning model's output. The adjudication is received and used to retrain the machine learning model. This process can iterate for a number of times to refine the machine learning model. For example, the number of iterations can be configured.

The method can also include applying the trained machine learning model to a new set of material candidates, the trained machine learning model outputting a subset of candidate material for polymerization.

The method can also include sorting the generated set of material candidates expected to yield materials with target properties and causing presenting of a predefined top number of the sorted material candidates to the subject matter expert for the subject matter expert to input the decision.

As described above, the machine learning model can include an artificial neural network, a convolutional neural network, a reinforcement neural network, random forest, support vector machine, and/or a logistic regression. As described above, the training data set for the machine learning model can include structured fingerprint data representation of molecular graphs. As described above, in an embodiment, the machine learning model is specific to the subject matter expert.

Figure 9:
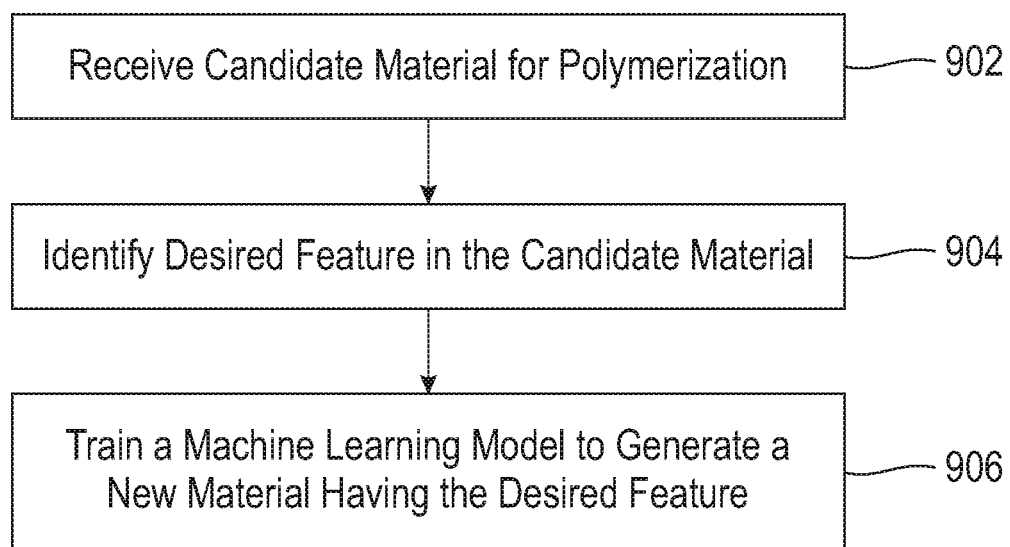
FIG. 9 is a diagram illustrating a method of polymer generation in an embodiment.

FIG. 9 is a diagram illustrating a method of polymer generation in one embodiment. The method can be implemented and/or performed on one or more hardware processors. The method in an embodiment generates one or more new monomers and/or polymers. At 902, the method can include receiving candidate material for polymerization. Examples of material include, but not limited to, molecules, monomers, and/or polymer repeat units. In an embodiment, the received candidate material can be those which are accepted or selected by a subject matter expert as being viable for polymerization. In another embodiment, the received candidate material can be those ranked by a classification model (e.g., 308 in FIG. 3) as likely candidates a subject matter expert would accept. For example, running such a trained classification model can automatically generate candidates, which can be ranked. At 904, the method can include identifying one or more desired features in the candidate material. For example, a Random Forest with a number of decision trees can be implemented to identifying the desired features. At 906, the method can include, based on the identified desired features, training a machine learning model to generate a new material having one or more of the desired features. By way of example, the machine learning model can be a GAN model, for example, a sequence generative adversarial deep neural network. In an embodiment, for example, optionally, the generated new material can be fed to a classification model ((e.g., 308 in FIG. 3) for ranking, for example, among other candidate material.

As described above, structured fingerprint data representation can be used to represent molecules or molecular components, e.g., monomers, polymers, for processing by a computer, for example, machine learning.

In an embodiment, e.g., optionally, the identified desired features can be presented or caused to be presented on a user interface, e.g., for user interaction or view. In an embodiment, a user (e.g., an SME) may select from the desired features, a desired feature to include in the new material being generated.

In a further embodiment, as described above with reference to FIG. 3, the machine learning model that generates new material can be implemented to include a specific feature in the new material being generated.

Figure 10:
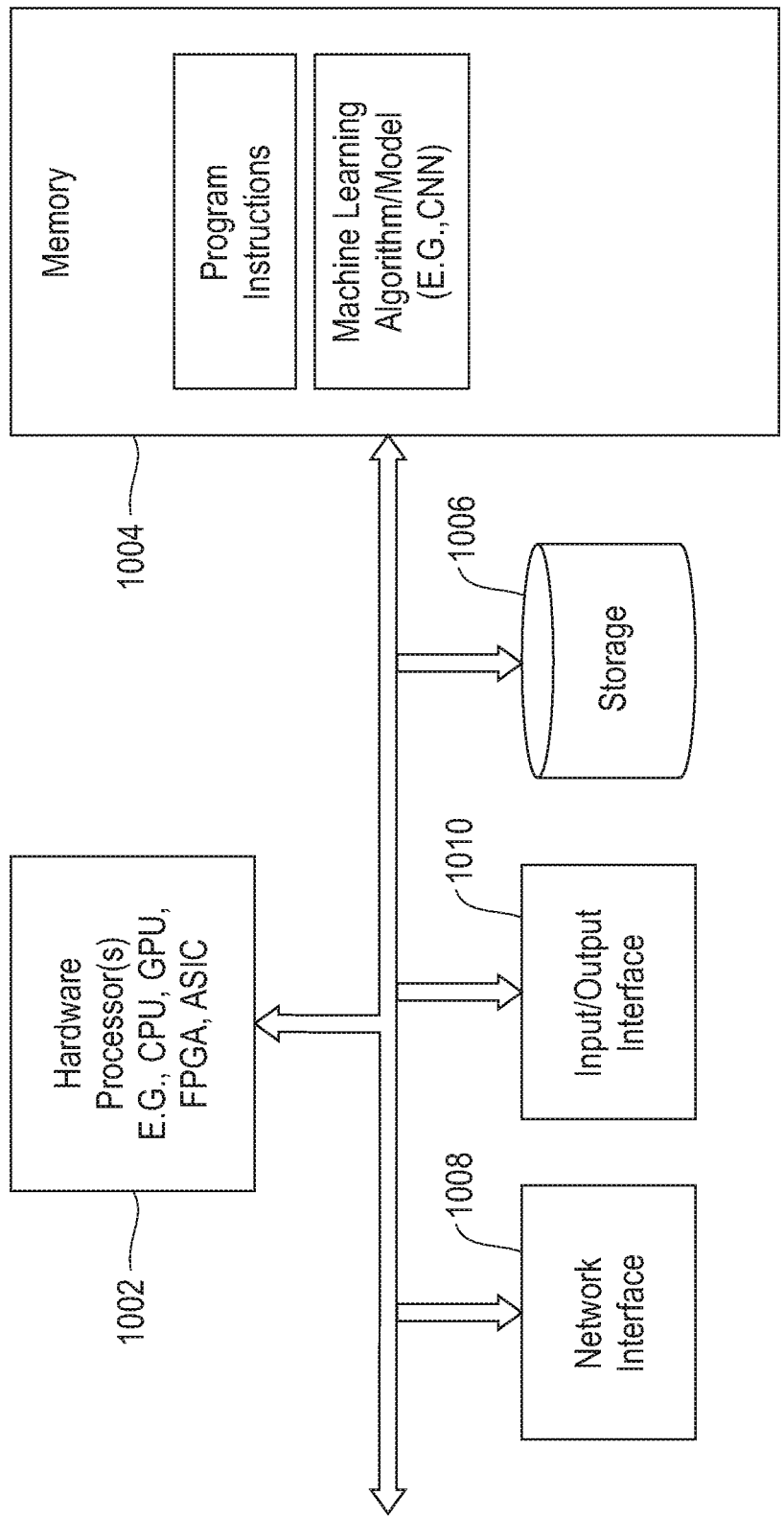
FIG. 10 is a diagram showing components of a system in an embodiment that performs polymer discovery.

FIG. 10 is a diagram showing components of a system in one embodiment that performs polymer discovery. One or more hardware processors 1002 such as a central processing unit (CPU), a graphic process unit (GPU), and/or a Field Programmable Gate Array (FPGA), an application specific integrated circuit (ASIC), and/or another processor, may be coupled with a memory device 1004, and generate a classification model, which can rank material candidates for polymerization. A memory device 1004 may include random access memory (RAM), read-only memory (ROM) or another memory device, and may store data and/or processor instructions for implementing various functionalities associated with the methods and/or systems described herein. One or more processors 1002 may execute computer instructions stored in memory 1004 or received from another computer device or medium. A memory device 1004 may, for example, store instructions and/or data for functioning of one or more hardware processors 1002, and may include an operating system and other program of instructions and/or data. For instance, at least one hardware processor 1002 may generate a set of material candidates expected to yield materials with target properties, receive subject matter expert's decision indicating accepted and rejected material candidates from the set of material candidates, and based on the subject matter expert's input, train a machine learning model to replicate the subject matter expert's decision. In one aspect, training data set may be stored in a storage device 1006 or received via a network interface 1008 from a remote device, and may be temporarily loaded into a memory device 1004 for building or generating the model. The learned model may be stored on a memory device 1004, for example, for execution by one or more hardware processors 1002. One or more hardware processors 1002 may be coupled with interface devices such as a network interface 1008 for communicating with remote systems, for example, via a network, and an input/output interface 1010 for communicating with input and/or output devices such as a keyboard, mouse, display, and/or others.

Figure 11:
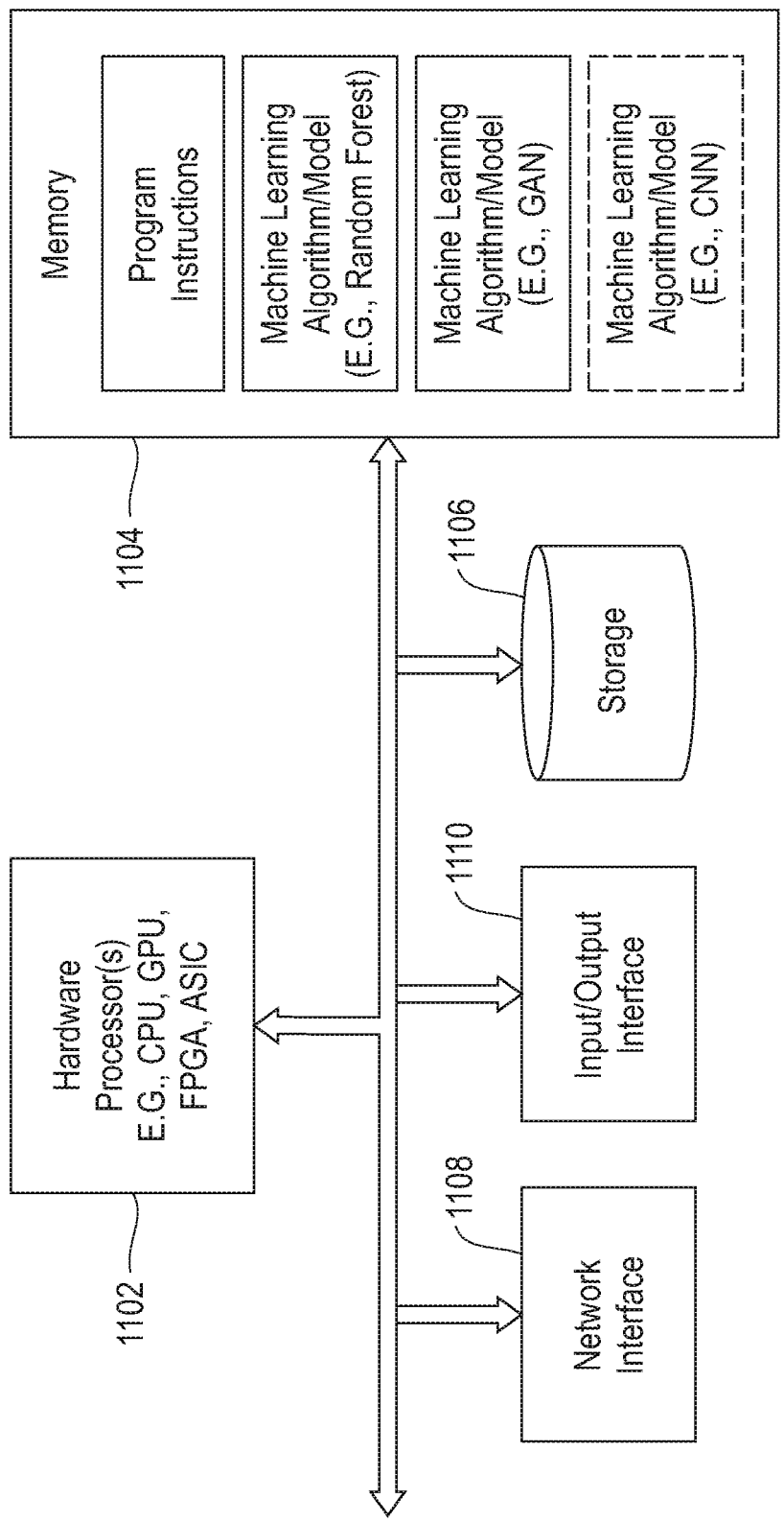
FIG. 11 is a diagram showing components of a system in an embodiment that performs polymer generation.

FIG. 11 is a diagram showing components of a system in one embodiment that performs polymer generation. One or more hardware processors 1102 such as a central processing unit (CPU), a graphic process unit (GPU), and/or a Field Programmable Gate Array (FPGA), an application specific integrated circuit (ASIC), and/or another processor, may be coupled with a memory device 1104, and build a machine learning model, which can generate new material. A memory device 1104 may include random access memory (RAM), read-only memory (ROM) or another memory device, and may store data and/or processor instructions for implementing various functionalities associated with the methods and/or systems described herein. One or more processors 1102 may execute computer instructions stored in memory 1102 or received from another computer device or medium. A memory device 1104 may, for example, store instructions and/or data for functioning of one or more hardware processors 1102, and may include an operating system and other program of instructions and/or data. For instance, at least one hardware processor 1102 may receive training data set which can include candidate material for polymerization, identify one or more desired features in the candidate material, and train a machine learning model to generate a new material having one or more of the desired features. In an embodiment, optionally, for example, the generated new material can be fed to a classification model for ranking. In one aspect, the training data set may be stored in a storage device 1106 or received via a network interface 1108 from a remote device, and may be temporarily loaded into a memory device 1104 for building or generating the model. The learned model may be stored on a memory device 1104, for example, for execution by one or more hardware processors 1102. One or more hardware processors 1102 may be coupled with interface devices such as a network interface 1108 for communicating with remote systems, for example, via a network, and an input/output interface 1110 for communicating with input and/or output devices such as a keyboard, mouse, display, and/or others.

Figure 12:
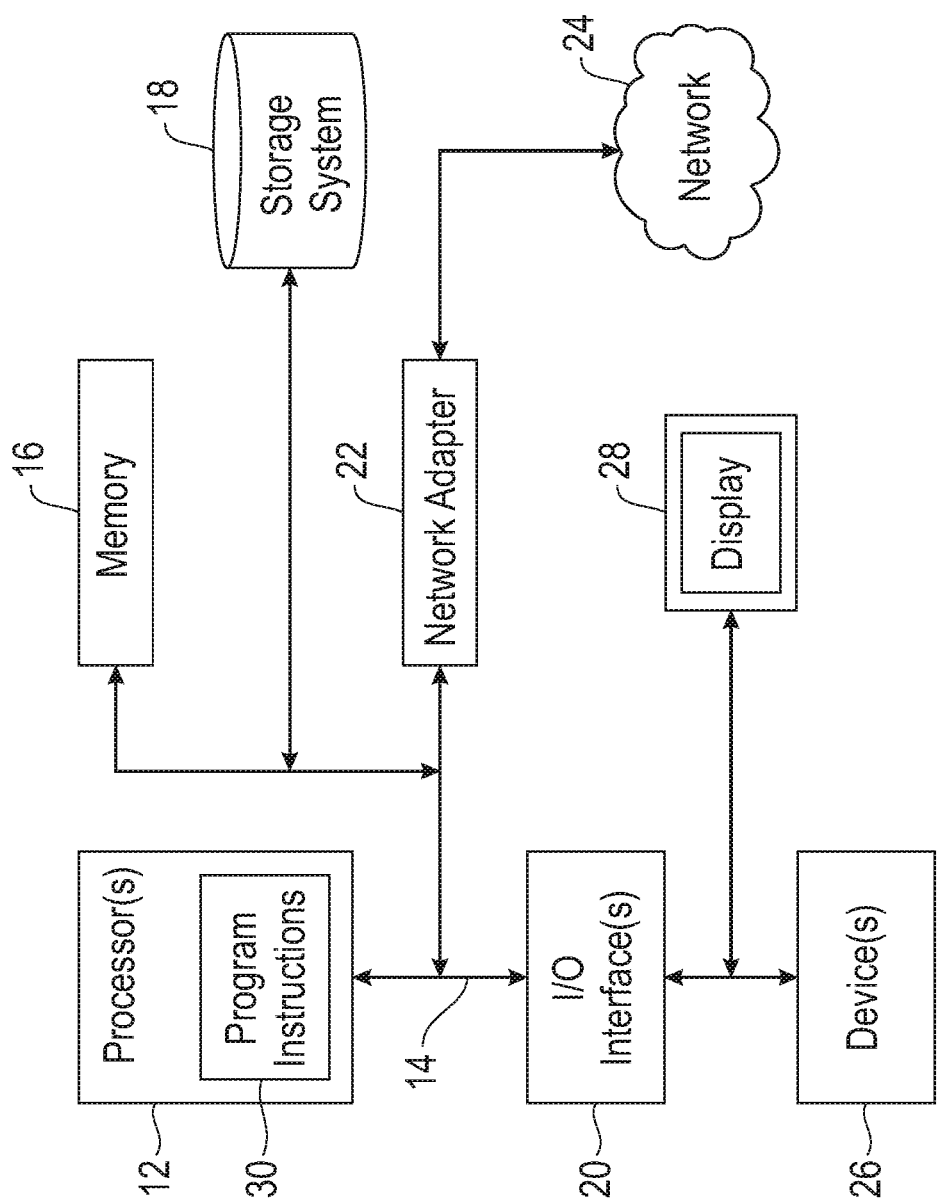
FIG. 12 illustrates a schematic of an example computer or processing system that may implement systems in embodiments.

FIG. 12 illustrates a schematic of an example computer or processing system that may implement systems in embodiments. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 12 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 30 that performs the methods described herein. The module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. As used herein, the term "or" is an inclusive operator and can mean "and/or", unless the context explicitly or clearly indicates otherwise. It will be further understood that the terms "comprise", "comprises", "comprising", "include", "includes", "including", and/or "having." when used herein, can specify the presence of stated features, integers, steps, operations, elements, and/or components, but do not preclude the presence or addition of one or more other features, integers, steps, operations, elements, components, and/or groups thereof. As used herein, the phrase "in an embodiment" does not necessarily refer to the same embodiment, although it may. As used herein, the phrase "in one embodiment" does not necessarily refer to the same embodiment, although it may. As used herein, the phrase "in another embodiment" does not necessarily refer to a different embodiment, although it may. Further, embodiments and/or components of embodiments can be freely combined with each other unless they are mutually exclusive.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method comprising:
    obtaining a first set of candidate materials for polymerization;
    inputting the first set of candidate materials into a machine learning classification model such that, in response, the machine learning classification model produces a ranking of the first set of candidate materials at least based on synthesizability;
    receiving, from at least one subject matter expert, one or more selections of individual candidate materials from the ranking;
    identifying at least one structural feature of the one or more selected individual candidate materials by at least feeding decomposed fragments of the one or more selected individuals candidate materials to a trained random forest model of decision trees trained to recognize patterns of the decomposed fragments;
    training a generative machine learning model on the selected one or more individual candidate materials, wherein a generator of the generative machine learning model generates new examples that follow example patterns in the selected one or more individual candidate materials, and a discriminator of the generative machine learning model receives as input at least one of the selected one or more individual candidate materials and at least one of the new examples and identifies which of the input is generated by the generator;
    using the trained generative machine learning model with a constraint that includes the identified at least one structural feature and with input of a first candidate material to generate data representative of a second candidate material that is different from the first candidate material; and
    interacting with the at least one subject matter expert via a user interface that presents a visual representation of the identified at least one structural feature, the visual representation being an artificial intelligence explanation.

2. The method of claim 1, further comprising generating the first set of candidate materials from a library of molecular fragments.

3. The method of claim 1, further comprising retraining the machine learning classification model using the data representative of the second candidate material.

4. The method of claim 1, further comprising training a random forest model of decision trees using structured fingerprint data representation of molecular graphs such that the random forest model becomes the trained random forest model of decision trees.

5. The method of claim 1, further comprising presenting the second candidate material on the user interface of a computer.

6. The method of claim 1, further comprising inputting the one or more selections of individual candidate materials into the machine learning classification model such that, in response, the machine learning classification model re-ranks the first set of candidate materials.

7. The method of claim 1, further comprising further training the generative machine learning model using candidate monomers selected by the at least one subject matter expert.

8. A computer system comprising:
a hardware processor; and
a memory device coupled with the hardware processor, the hardware processor configured to at least:
obtain a first set of candidate materials for polymerization;
input the first set of candidate materials into a machine learning classification model such that, in response, the machine learning classification model produces a ranking of the first set of candidate materials at least based on synthesizability;
receive, from at least one subject matter expert, one or more selections of individual candidate materials from the ranking;
identify at least one structural feature of the one or more selected individual candidate materials by at least feeding decomposed fragments of the one or more selected individuals candidate materials to a trained random forest model of decision trees trained to recognize patterns of the decomposed fragments;
train a generative machine learning model on the selected one or more individual candidate materials, wherein a generator of the generative machine learning model generates new examples that follow example patterns in the selected one or more individual candidate materials, and a discriminator of the generative machine learning model receives as input at least one of the selected one or more individual candidate materials and at least one of the new examples and identifies which of the input is generated by the generator;
use the trained generative machine learning model with a constraint that includes the identified at least one structural feature and with input of a first candidate material to generate data representative of a second candidate material that is different from the first candidate material; and
interact with the at least one subject matter expert via a user interface that presents a visual representation of the identified at least one structural feature, the visual representation being an artificial intelligence explanation.

9. The computer system of claim 8, wherein the hardware processor is further configured to generate the first set of candidate materials from a library of molecular fragments.

10. The computer system of claim 8, wherein the hardware processor is further configured to retrain the machine learning classification model using the data representative of the second candidate material.

11. The computer system of claim 8, wherein the hardware processor is further configured to train a random forest model of decision trees using structured fingerprint data representation of molecular graphs such that the random forest model becomes the trained random forest model of decision trees.

12. The computer system of claim 8, wherein the hardware processor is further configured to present the second candidate material on the user interface of a computer.

13. The computer system of claim 8, wherein the hardware processor is further configured to input the one or more selections of individual candidate materials into the machine learning classification model such that, in response, the machine learning classification model re-ranks the first set of candidate materials.

14. The computer system of claim 8, wherein the hardware processor is further configured to train the generative machine learning model using candidate monomers selected by the at least one subject matter expert.

15. A computer program product comprising a non-transitory computer readable storage medium having program instructions embodied therewith, the program instructions executable by a computer to cause the computer to:
obtain a first set of candidate materials for polymerization;
input the first set of candidate materials into a machine learning classification model such that, in response, the machine learning classification model produces a ranking of the first set of candidate materials at least based on synthesizability;
receive, from at least one subject matter expert, one or more selections of individual candidate materials from the ranking;
identify at least one structural feature of the one or more selected individual candidate materials by at least feeding decomposed fragments of the one or more selected individuals candidate materials to a trained random forest model of decision trees trained to recognize patterns of the decomposed fragments;
train a generative machine learning model on the selected one or more individual candidate materials, wherein a generator of the generative machine learning model generates new examples that follow example patterns in the selected one or more individual candidate materials, and a discriminator of the generative machine learning model receives as input at least one of the selected one or more individual candidate materials and at least one of the new examples and identifies which of the input is generated by the generator;
use the trained generative machine learning model with a constraint that includes the identified at least one structural feature and with input of a first candidate material to generate data representative of a second candidate material that is different from the first candidate material; and
interact with the at least one subject matter expert via a user interface that presents a visual representation of the identified at least one structural feature, the visual representation being an artificial intelligence explanation.

16. The computer program product of claim 15, wherein the program instructions are executable by the computer to further cause the computer to generate the first set of candidate materials from a library of molecular fragments.

17. The computer program product of claim 15, wherein the program instructions are executable by the computer to further cause the computer to retrain the machine learning classification model using the data representative of the second candidate material.

18. The computer program product of claim 15, wherein the program instructions are executable by the computer to further cause the computer to train a random forest model of decision trees using structured fingerprint data representation of molecular graphs such that the random forest model becomes the trained random forest model of decision trees.

19. The computer program product of claim 15, wherein the program instructions are executable by the computer to further cause the computer to present the second candidate material on the user interface of a computer.

20. The computer program product of claim 15, wherein the program instructions are executable by the computer to further cause the computer to input the one or more selections of individual candidate materials into the machine learning classification model such that, in response, the machine learning classification model re-ranks the first set of candidate materials.

* * * * *